United States Patent [19]

Wilkinson et al.

[11] Patent Number: 4,851,836
[45] Date of Patent: Jul. 25, 1989

[54] AUDIO-TACTILE PEDESTRIAN PUSH BUTTON SIGNALLING SYSTEM

[75] Inventors: Barry N. Wilkinson, Waverley; Barrie J. Holst, Rydalmere, both of Australia

[73] Assignee: Amalgamated Wireless Limited, Sydney, Australia

[21] Appl. No.: 165,270

[22] PCT Filed: Apr. 28, 1987

[86] PCT No.: PCT/AU87/00114

§ 371 Date: Feb. 1, 1988

§ 102(e) Date: Feb. 1, 1988

[87] PCT Pub. No.: WO87/06751

PCT Pub. Date: Nov. 5, 1987

[30] Foreign Application Priority Data

Apr. 29, 1986 [AU] Australia .................. PH5653

[51] Int. Cl.⁴ ............................................. G08B 1/095
[52] U.S. Cl. ............................. 340/944; 340/407
[58] Field of Search ............... 340/944, 925, 407, 75, 340/88, 326, 107, 825.46; 40/612, 613

[56] References Cited

U.S. PATENT DOCUMENTS 2,461,448 2/1948 Smith ................................ 340/84
4,253,083 1/1981 Imamura ......................... 340/944

FOREIGN PATENT DOCUMENTS 2816683 10/1979 Fed. Rep. of Germany .
3138431A1 5/1983 Fed. Rep. of Germany .
2375672 7/1978 France .
2481491 10/1981 France .
2011145 12/1978 United Kingdom .

OTHER PUBLICATIONS

By T. Poulsen, "Acoustic Traffic Signal for Blind Pedestrians", 15 Applied Acoustics 363-376 (1982).

Primary Examiner—Joseph A. Orsino
Assistant Examiner—Jeffery A. Hofsass
Attorney, Agent, or Firm—Leydig, Voit & Mayer

[57] ABSTRACT

An audio-tactile pedestrian signalling system for use in conjunction with traffic control signal installation having a transducer (16) providing audio and tactile signals by means of signal generator (11, 12, 13, 14). The transducer acts as a microphone to provide a feedback signal to an automatic gain control circuit (19) to adjust the signal to noise level ratio with respect to ambient traffic noise.

19 Claims, 1 Drawing Sheet

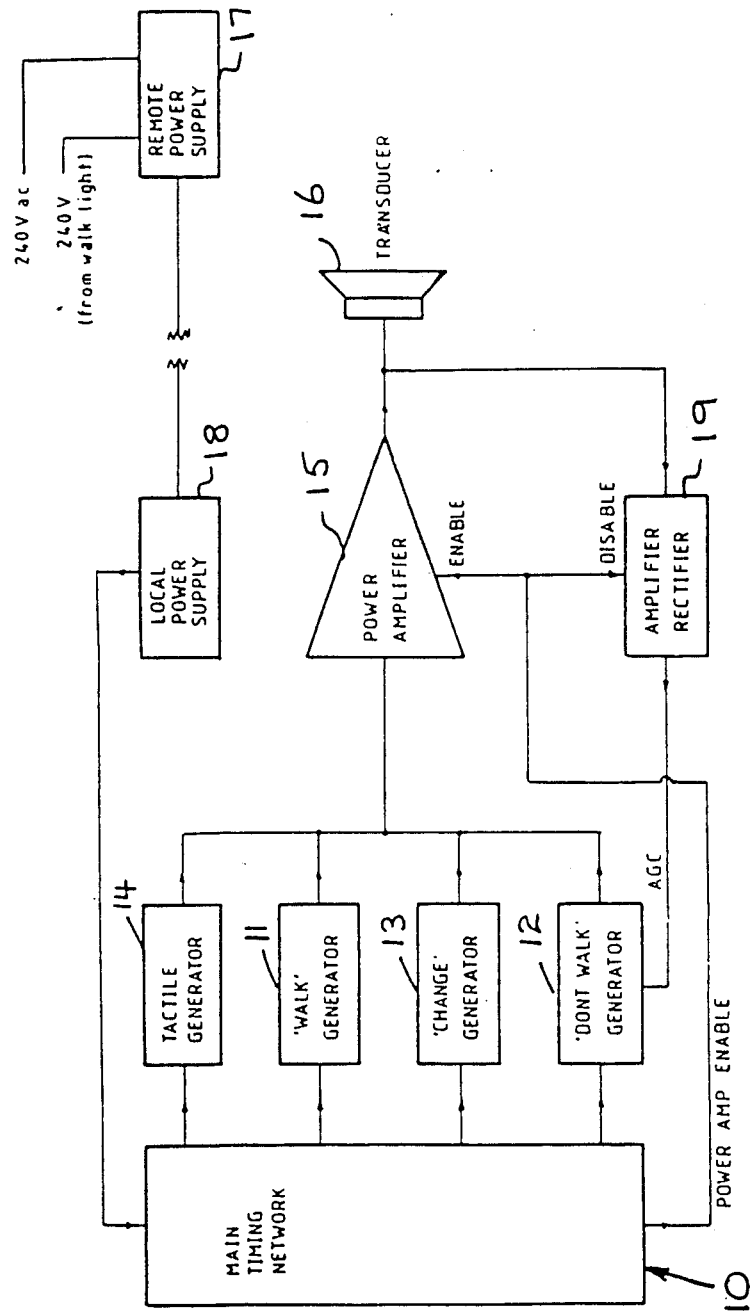

AUDIO-TACTILE PEDESTRIAN PUSH BUTTON SIGNALLING SYSTEM

FIELD OF INVENTION

This invention relates to audio-tactile pedestrian push-button signalling systems for use in conjunction with traffic control signal installations.

BACKGROUND ART

An audio-tactile traffic signalling system provides combined audible and tactile signals to supplement the normal pedestrian light signals at controlled pedestrian crossings. Two types of audio-tactile signals are provided:

(a) a locating signal which enables the visually handicapped person to locate the push-button assembly and register a demand. This signal is continuously emitted except when the associated pedestrian light signal is green, (b) a crossing signal which is emitted only when the associated pedestrian light signal is green.

The tranducer for the audio-tactile signal is located within the push-button assembly and acts on the front surface of the push-button housing. The associated electronic equipment to drive the tranducer is contained in a separate housing remote from the push-button assembly, for example, adjacent to the traffic lights. The remote driver unit or housing is hard-wired to the transducer in the push-button assembly.

The audible locating signal as defined by the Department of Main Road of New South Wales, Australia specification ATS/2 has the following operational characteristics:

(a) a fundamental frequency within the range 900 Hz to 1100 Hz;
(b) a spectral bandwidth extending to at least 5 kHz;
(c) a rectangular waveform with a rectangular modulation envelope of between 20 ms and 30 ms duration;
(d) a pulse repetition frequency within the range of 0.5 to 0.6 Hz;
(e) an output sound pressure level which is automatically adjusted to maintain a constant relationship with the instantaneous A-weighted ambient noise level over the range 35 to 75 dB (A); and
(f) fixed upper and lower output sound pressure levels which are maintained when the ambient noise is outside the range specified in (e) above.

In order to comply with requirement (e), a microphone is mounted within the remote driver unit or housing to monitor the ambient noise level and to provide a suitable control signal.

The audible crossing signal as defined by the above specification ATS/2 has two separate stages:

(a) an initial transition stage comprising a single pulse of a constant amplitude square wave having a frequency changing exponentially from 2 kHz to 500 Hz with a time constant of 50 ms; and
(b) a second stage having the following operational characteristics:
  (i) a fundamental frequency of between 400 Hz and 600 Hz;
  (ii) a spectral bandwidth extending to at least 5 kHz;
  (iii) a sinusoidal waveform with an amplitude decaying exponentially with a time constant of 50 ms; and
  (iv) a pulse repetition frequency within the range 8 Hz to 10 Hz.

The tactile signal generated on the front of the push button assembly housing is defined by specification ATS/2 as follows:

(a) the area over which the tactile signal is generated shall be at least 30 mm diameter located immediately above the push-button switch, using a pedestrian push-button switch assembly complying with specification No. PB/5.
(b) the tactile signal shall have a sinusoidal waveform with a frequency lying between 100 Hz and 175 Hz.
(c) the tactile signal shall be in-phase with the audible signals specified under Clauses 3.2 and 3.3. The signal shall comprise an integral number of cycles (between 3 and 8) commencing and finishing on a zero crossing, with a duration of not less than 30 milliseconds and periodicity corresponding to the audible signal.
(d) the tactile signal output shall have a peak acceleration exceeding 1 g (9.81 m/s$^2$). This will necessitate an output voltage in the range 8 to 11 V peak-to-peak, depending upon frequency, for the nominal sensitivity of the transducer specified in FIG. 2.

The remote driver unit or housing contains two isolating transformers connected to:

(a) a nominal 240 volt AC mains supply, and,
(b) the nominal 240 volt AC active feed to the associated pedestrian green signal lamps, for operation of the audio-tactile tranducer as well as the associated electronic circuits.

Although the applicant's prior art audio-tactile traffic signalling system of the kind described above has achieved wide commercial acceptance, there is a need for an improved system which is simpler in constructional detail and cheaper to produce.

DISCLOSURE OF INVENTION

An audio-tactile pedestrian push-button signalling system according to the present invention includes a housing, signal generator means having an Automatic Gain Control circuit within the housing, a tranducer within the housing operative under the control of the signal generating means to produce pre-determined audio and tactile signals, said transducer being adapted to act as a responsive microphone so as to provide a feedback signal to the Automatic Gain Control circuit for adjusting the signal to noise level ratio with respect to ambient traffic noise.

The mounting of the signal generator means and the transducer within the pedestrian push-button housing obviates the need for an additional driver unit or housing as is required by prior art systems. Line tranformers may be mounted within the associated pedestrian signal lanterns which would be advantageous in that it would segregate the low voltage and extra low voltage levels.

In a preferred form of the invention, the push-button housing and actuator are manufactured by injection moulding techniques from high grade engineering plastics such as polycarbonate or glass-filled nylon. The use of an injected moulded housing obviates the need for machining, degreasing and painting as is the case with the current aluminium cast housing.

The signal generator means incorporates thick film hybrid micro electronics which reduces the area required to house the electronic circuitry so it may be located within the pedestrian push-button rather than in a separate driver unit housing.

A compact signal tranducer is designed to produce the correct audible and tactile signals at the appropriate levels. The transducer also acts as a responsive microphone and is capable of providing the required feedback to operate the Automatic Gain Control circuit so as to adjust the signal to noise level ratio with respect to ambient traffic noise. Such a tranducer eliminates the need for the microphone used in present audio-tactile signalling systems.

The audio-tactile signal generator system is driven by a single line transformer which is mounted within the associated pedestrian signal lantern. The input to the signal generator is so arranged, and the line transformer so switched, to differentiate via half and full wave alternating current switching in order to produce the locating and crossing signals with full failsafe backup.

The audio-tactile signal generator also produces a visual indication to the pedestrian, to advise that the button has been previously pressed and the crossing signal (as movement) will be serviced by the controller in cyclic order.

BRIEF DESCRIPTION OF THE DRAWING

In order that the invention may be more readily understood and put into practical effect, reference will now be made to the accompanying drawing which is a schematic diagram of a signal system for an audio-tactile pedestrian push-button according to an embodiment of the invention.

BEST MODE OF CARRYING OUT THE INVENTION

The signalling system shown in the drawing includes a main timing network 10 which controls four separate tone generators namely:

(a) WALK tone generator 11 which is adapted to produce a 500 Hz decaying sinewave,
(b) DON'T WALK tone generator 12 which is adapted to produce 32 cycles of a 1 kHz square wave,
(c) CHANGE tone generator 13 which is adapted to produce a square wave burst starting at about 2 kHz and dropping to 500 Hz over a 50 millisecond period,
(d) TACTILE tone generator 14 which is adapted to produce 4 cycles of a 128 Hz sinewave.

The output of each of the tone generators 11,12,13 and 14 is applied to power amplifier 15 which drives the transducer 16. The main power supply unit 17 is remote from the transducer 16, being either at the top of the traffic light pole (not shown) or at the main control box (also not shown) for the system.

The power supply unit 17 provides an extra low A.C. votage which is half wave during the DON'T WALK mode and full wave during the WALK mode. Thus, only two wires are needed to power and control the system. The local power supply unit 18 within the pedestrian push-button housing rectifies the A.C. signal from the power supply unit 17 to provide the D.C. voltages required. The local power supply unit 18 also decodes the full wave/half wave signal to provide the WALK and DON'T WALK signals to the main timing network 10.

The sound transducer 16 is constituted by the circular aluminium plate normally used in the push-button assembly as the direction arrow indicator. The transducer 16 is vibrated by a loudspeaker style magnet and voice coil assembly. The transducer 16 is also used as the microphone for the automatic volume control in the DON'T WALK mode.

The power amplifier 15 has an output DISABLE control to allow the transducer 16 to be used as the microphone during the time between pulses in the DON'T WALK signal. The microphone output of the transducer 16 is applied to amplifier/rectifier 19 to give a D.C. signal which automatically controls the gain of the DON'T WALK signal. The network 10 has a disable control to prevent it from being swamped by the power amplifier when it is active.

The tone generators 11,12,13 and 14 are controlled by the main timing circuit 10 so that in the DON'T WALK mode the tactile tone is repeated every 2 seconds followed immediately by the DON'T WALK tone burst to provide an audible locating signal and a slow tactile signal indicating not to walk.

When the WALK light comes on, the CHANGE tone sounds once to attract attention and then the WALK tone is repeated eight times per second. The difference in tone and repetition rate gives the audible WALK signal while the high level tone acts as the tactile component with the repetition rate being the determining factor.

Various modifications may be made in details of design and construction without departing from the scope and ambit of the invention.

We claim:

1. An audio-tactile pedestrian push-button signalling system comprising signal generator means having an automatic gain control circuit, a transducer operative under the control of the signal generator means to produce predetermined audio and tactile signals, means for adapting said transducer to act as a responsive microphone so as to provide a feedback signal to said automatic gain control circuit for adjusting a signal-to-noise level ratio of said system with respect to ambient traffic noise and powering said system by a single line from a remote power supply, said single line carrying a power signal which alternates between at least first and second modes in response to the "WALK"/"DON'T WALK" status of an associated conventional pedestrian signalling system.

2. A signalling system as set forth in claim 1 and further including a timing network responsive to said first and second modes of said power signal to actuate said signal generator means to provide WALK, CHANGE and DON'T WALK audio tones and tactile signals in a predetermined sequence.

3. A signalling system as set forth in claim 2 and further including a power amplifier coupling said signal generator means to said generator.

4. A signalling system according to any one of claims 2 or 3 and including a power supply circuit connected between said single line and said signal generator means and operative to decode said first and second modes of said power signal to provide WALK and DON'T WALK signals to said timing network.

5. A signalling system as set forth in claim 4 wherein said first mode is half-wave waveform of said power signal and said second mode is a full-wave waveform of said power signal.

6. A signalling system as set forth in claim 3 and including means to limit the operation of said transducer as a microphone to times between pulses of said DON'T WALK tone.

7. A signalling system as set forth in claim 2 wherein said signal generator means is responsive to said timing network to provide during the generation of said DON'T WALK tone a low-frequency signal which is repeated on a regular basis followed by said DON'T WALK tone so as to provide an audible locating tone and a tactile signal.

8. A signalling system according to claim 7 wherein said signal generator means provides said CHANGE tone when said first mode is generated by said power signal, followed by said WALK tone repeated on a regular basis, thereby creating both audible and tactile signals.

9. A signalling system as set forth in claim 1 wherein said transducer is coupled to said signal generating means through an amplifier rectifier.

10. An audio-tactile pedestrian push-button signalling system comprising the following:
   signal generating means generating signals of at least first and second frequencies;
   a unitary transducer element responsive to said signal generator means for functioning as a speaker to create (1) an audio signal in response to said signal of said first frequency and (2) tactile signal in response to said signal of said second frequency;
   first means for detecting an ambient noise level and adjusting said signal generating means in response thereto so as to ensure said audio signal may be heard by blind pedestrians; and
   a timing network for controlling the application of said at least first and second frequencies to said transducer element and including second means for disabling said unitary transducer element from responding to said signal generator means so as to allow said transducer element to function as a microphone to convert ambient noise to electrical signals for said first means such that said speaker and microphone functions of said unitary transducer element are time interleaved.

11. A signalling system as set forth in claim 10 including means responsive to a bi-state signal from a traffic control mechanism for synchronizing said timing network with said traffic control mechanism.

12. A signalling system as set forth in claim 11 wherein said signal generator means includes means responsive to said timing network for providing a first signal mode to said unitary transducer element indicative of an audio WALK signal and a second signal mode to said unitary transducer indicative of an audio DON'T WALK signal.

13. A signalling system as set forth in claim 12 including means coupling said disabling means and said timing means such that said disabling means and said timing means cooperate to cause said unitary transducer element to function as a microphone between pulses comprising said second signal mode.

14. A signalling system as set forth in claim 13 wherein said first signal mode is a half-wave signal and said second signal mode is a full-wave signal.

15. A signalling system as set forth in claim 13 wherein said second signal mode includes a signal for vibrating said unitary transducer element in a manner which provides a tactile signal.

16. A signalling system as set forth in claim 15 wherein said first signal mode causes said unitary transducer element to generate a CHANGE tone to attract the attention of said blind pedestrian followed by a WALK signal repeated a predetermined number of times per second so as to create a tactile signal at said unitary transducer element.

17. A signalling system as set forth in claim 10 wherein said detecting means is an amplifier rectifier responsive to said timing network to provide an automatic gain control signal to said signal generator means in responsive to said electrical signals from said unitary transducer element.

18. A signalling system as set forth in claim 10 including a coupling between said system and a conventional pedestrian signalling system which is comprised of a single line that serves both as a power source and as a means to synchronize the operation of said two systems.

19. A signalling system as set forth in claim 10 wherein said disabling means includes a power amplifier coupling said signal generator means to said unitary transducer element.

* * * * *